US008657819B2

United States Patent
Mürner et al.

(10) Patent No.: US 8,657,819 B2
(45) Date of Patent: Feb. 25, 2014

(54) EASY TO CLEAN CLAMPING DEVICE (75) Inventors: Beat Mürner, Reichenbach (CH);
Robert Wider, Derendingen (CH);
Roland Thomke, Bellach (CH)

(73) Assignee: Stryker Trauma SA (CH)

( * ) Notice: Subject to any disclaimer, the term of this patent is extended or adjusted under 35 U.S.C. 154(b) by 197 days.

(21) Appl. No.: 12/879,382

(22) Filed: Sep. 10, 2010

(65) Prior Publication Data

US 2011/0087226 A1 Apr. 14, 2011

(30) Foreign Application Priority Data

Sep. 11, 2009 (EP) .................................. 09170105

(51) Int. Cl.
*A61B 17/00* (2006.01)
(52) U.S. Cl.
USPC .......................................................... 606/54
(58) Field of Classification Search
USPC ............. 606/54–59, 324, 277, 278; 411/349, 411/549, 553; 403/385, 348–349
See application file for complete search history.

(56) References Cited

U.S. PATENT DOCUMENTS

| D255,713 | S | | 7/1980 | Sturges | |
|---|---|---|---|---|---|
| 4,620,533 | A | | 11/1986 | Mears | |
| 4,941,481 | A | * | 7/1990 | Wagenknecht | 606/59 |
| 5,380,325 | A | * | 1/1995 | Lahille et al. | 606/250 |
| 5,624,440 | A | * | 4/1997 | Huebner | 606/59 |
| 5,746,741 | A | | 5/1998 | Kraus et al. | |
| 5,752,954 | A | | 5/1998 | Mata et al. | |
| 5,800,022 | A | * | 9/1998 | Del Rosario | 301/5.306 |
| 6,080,153 | A | | 6/2000 | Mata et al. | |
| 6,261,042 | B1 | * | 7/2001 | Pratt | 411/551 |
| D455,831 | S | | 4/2002 | Koros et al. | |
| 6,520,962 | B1 | | 2/2003 | Taylor et al. | |
| 6,579,030 | B2 | * | 6/2003 | Uhler et al. | 403/348 |
| 6,616,664 | B2 | | 9/2003 | Walulik et al. | |
| 6,702,814 | B2 | | 3/2004 | Walulik et al. | |
| 6,837,645 | B2 | * | 1/2005 | Kanatani et al. | 403/348 |
| 6,916,319 | B2 | | 7/2005 | Munting | |
| D526,410 | S | | 8/2006 | Phillips et al. | |

(Continued)

FOREIGN PATENT DOCUMENTS

| CH | 657899 A5 | 9/1986 |
|---|---|---|
| DE | 518329 C | 2/1931 |

(Continued)

*Primary Examiner* — Jan Christopher Merene
(74) *Attorney, Agent, or Firm* — Lerner, David, Littenberg, Krumholz & Mentlik, LLP (57) ABSTRACT An easy to clean clamping device has at least one clamping assembly having two jaws. The jaws form at least one recess to accommodate an element to be clamped along the longitudinal axis of the recess. A locking unit is provided to allow closing of the jaws against the force of a spring element. The locking unit has a shaft extending along an axis and through bores of the jaws. The shaft has a head for operating the clamping action abutting against the uppermost jaw. A locking element is provided having a through bore and which locking element can be arranged between the head and the uppermost jaw. One portion of the locking unit has a larger diameter than the bore of the second jaw and the head of the locking unit has a smaller diameter than the bore of the adjacent jaw. The locking element comprises at least one locking surface which can be brought into positive locking with a corresponding surface of the head for blocking removal of the locking element.

15 Claims, 8 Drawing Sheets

(56) References Cited

U.S. PATENT DOCUMENTS

| | | |
|---|---|---|
| D537,939 S | 3/2007 | Phillips et al. |
| D551,763 S | 9/2007 | Phillips et al. |
| 7,562,855 B2 | 7/2009 | Oetlinger |
| 8,241,285 B2 * | 8/2012 | Mullaney .................. 606/59 |
| 2002/0077629 A1 | 6/2002 | Hoffman et al. |
| 2003/0199738 A1 * | 10/2003 | Yager ........................ 600/227 |
| 2004/0044344 A1 | 3/2004 | Winquist et al. |
| 2005/0240265 A1 | 10/2005 | Kuiper et al. |
| 2006/0025703 A1 | 2/2006 | Miles et al. |
| 2006/0039750 A1 | 2/2006 | Thomke et al. |
| 2006/0052785 A1 | 3/2006 | Augostino et al. |
| 2006/0167453 A1 | 7/2006 | Hoffmann-Clair et al. |
| 2006/0177263 A1 * | 8/2006 | Thomke et al. ............ 403/322.4 |
| 2008/0215053 A1 | 9/2008 | Thomke et al. |
| 2008/0306527 A1 | 12/2008 | Winslow et al. |
| 2009/0018541 A1 * | 1/2009 | Lavi ............................... 606/59 |
| 2009/0088751 A1 | 4/2009 | Mullaney |
| 2010/0298827 A1 * | 11/2010 | Cremer et al. .................. 606/54 |
| 2011/0087226 A1 | 4/2011 | Murner et al. |

FOREIGN PATENT DOCUMENTS

| | | |
|---|---|---|
| DE | 10246418 A1 | 4/2004 |
| EP | 0700664 A1 | 3/1996 |
| EP | 1920720 A1 | 5/2008 |
| JP | 2003325058 A | 11/2003 |

* cited by examiner

EASY TO CLEAN CLAMPING DEVICE

CROSS-REFERENCE TO RELATED APPLICATION

The present application claims the benefit of European Patent Application No. 09 170 105.2, filed Sep. 11, 2009, entitled Easy To Clean Clamping Device, the disclosure of which is hereby incorporated herein by reference.

BACKGROUND OF THE INVENTION

The present invention relates to an easy to clean clamping device and more particularly to a fixation clamp for use in an external fixation system for holding bone fragments adjacent to each other.

U.S. Pat. No. 5,242,240 relates to a clamping device for a surgical retractor and is concerned with cleansing and sterilization problems. It is mentioned that problems occur when components of such a device are lost or misplaced and therefore the clamping device is combined with retaining elements to maintain the device in a fully assembled state even for cleansing operations.

U.S. Pat. No. 6,277,069 relates to a clamp using a lever which opens the clamping jaws along the shaft which allows opening of the jaws. This is a solution allowing better cleansing of the parts between the jaws without losing device parts. However, this clamping device does not have a very complex design.

Furthermore prior art documents recommend that for complicated devices, as shown in WO 2005/096966, it is preferred to allow for easy disassembly for cleaning and sterilization purposes. According to this document it is an object of the industry to provide new devices having fewer components than existing devices so that simple operation and cleaning is more readily possible.

However, new clamps, especially for external fixation systems are designed for improved handling and therefore more complicated and disassembly is not a solution.

BRIEF SUMMARY OF THE INVENTION

It is therefore one aspect of the invention to overcome the cleansing and sterilization problems of the prior art devices and to provide the practitioner with a clamping device especially for use in an external fixation system, which device can easily be cleaned and sterilized without the risk of losing important parts of the device or losing time for the re-assembly. It is noted by the inventors that a clamping device of this kind comprises a central shaft around which clamping jaws are arranged. These elements together with a central spring are valuable parts of the device. However this structure makes it difficult to attend to cleansing of the interstitial between two jaws of one clamping assembly and also in the case of two clamping assemblies between one jaw and another of the same assembly as well as between the central shaft and the different jaw parts, especially in view of a spring element.

The invention is based on the insight that beside the above mentioned important parts of a clamp it is possible to provide one locking portion allowing withdrawal of simply one part of a jaw. This avoids the risk of losing important parts of the device but nevertheless allows a spreading of the remaining parts along the central shaft, i.e. allow an easy accessibility of the one or more remaining jaw parts and a spring element allowing the clamping function.

Usually such clamping devices for external fixation devices exist in a plurality of different sizes. Since it is only possible to take away one jaw portion from the central shaft arrangement, this avoids mixing of different device parts. It is especially an advantage of the invention that the locking element can be the same for a plurality of clamping devices so that they can readily be exchanged. Additionally, if one of these smaller sized parts is lost it can readily and at least cost be replaced, since the locking element is preferably used in one or few standardized sizes.

A clamping device for use in an external fixation system for holding bone fragments adjacent to each other with the help of fixation elements has at least one clamping assembly having two jaws. The jaws provide at least one recess to accommodate a rod element to be clamped along the longitudinal axis of the recess. A locking unit is provided having a shaft with a head. A spring element is positioned between two of the jaws. A locking element having a through bore is located between the head and a first jaw. Each of the jaws has a through bore to accommodate the shaft extending through the through bores of the jaws. The first jaw is the jaw of the at least two jaws being positioned adjacent to the head of the locking shaft. The head of the locking shaft is adapted for operating the clamping action by applying a force against the first jaw to allow the jaws to close against the force of the spring element. The head of the locking unit has a larger diameter than the through bore of a second jaw, wherein the head of the locking shift has a smaller diameter than at least the through bore of the first jaw. The locking element has at least one locking surface which can be brought into positive locking with a corresponding surface of the head for blocking removal of the locking element. A portion of the head of the locking unit has a larger diameter than the bore of the second jaw. The locking unit may have a portion separate and beyond the head which portion has the larger diameter than the bore of the second jaw and the head has a smaller diameter than the bore. At least one locking surface of the locking element comprises an adjacent wall parallel to the axis of the device and providing an actuation height for disengaging a positive lock with the head. The at least one locking surface comprises two or three locking surfaces within an angular spacing of 180 or 120 degree, respectively. The locking element comprises two or three passage allowing surfaces within an angular spacing of 180 or 120 degree, respectively so that it may be removed from the head. The locking element may have a side opening and wherein the locking surface on the locking element may comprise a circular locking rim and an adjacent side wall providing the actuation height for disengaging the positive locking with the locking unit. The side opening may have parallel side walls defining its mouth and having a diameter smaller than the diameter of the shaft of the locking unit. The locking unit comprises an actuator screw and a blocking element, wherein the actuator screw comprises a connection interface for a corresponding interface of the blocking element. The blocking element comprises a shaft adapted to be mounted in prolongation of the shaft of screw and comprising a flange having a larger diameter than the bore of the second jaw and/or of the third jaw of the clamping assemblies.

A clamping device for use in an external fixation system has a first and second jaw and a locking unit comprising a shaft extending through a bore in the first jaw and a bore in the second jaw. The shaft of the locking unit has a head, a diameter of the head being smaller than a diameter of the bore in the first jaw and larger than a diameter of the bore in the second jaw. The first jaw is positioned closer to the locking unit head than the second jaw. A locking element is located between the head and the first jaw. The locking element has an opening for receiving the shaft and a coupling element for selectively engaging and disengaging the locking element from the locking unit so that the first jaw can be removed from the shaft. The head of the locking unit has a coupling element engaged with a coupling element on the locking element in a first rotational position around the shaft and disengaged from the locking element coupling element in a second rotational position.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
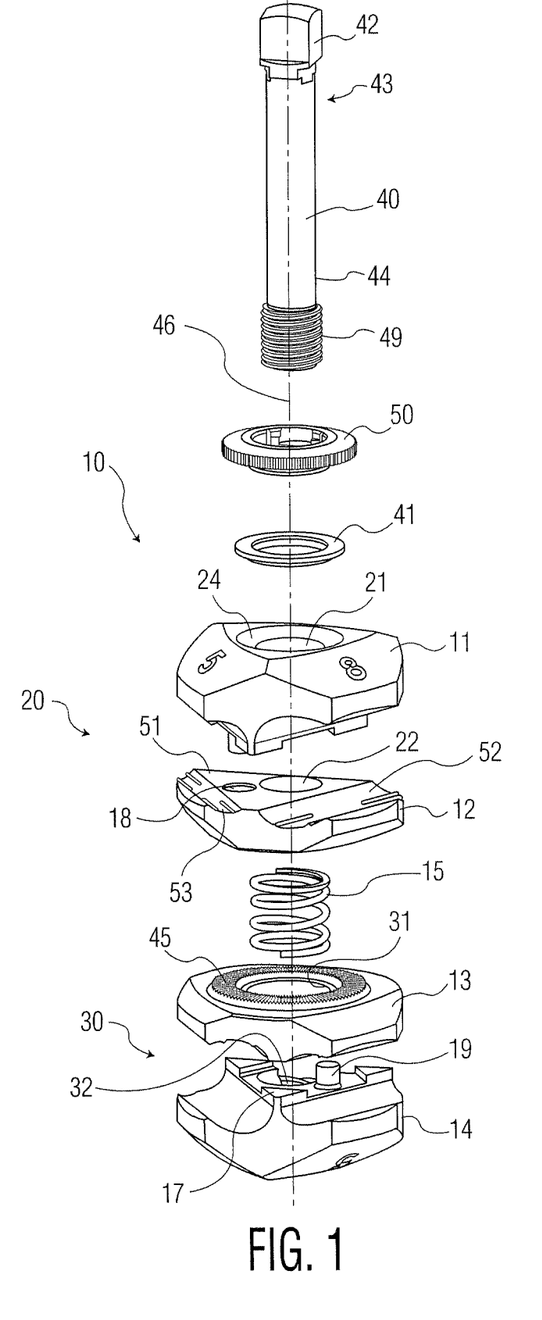
FIG. 1 shows an exploded view of a first embodiment of the clamp of the present invention.

FIG. 1 shows a perspective exploded view of a preferred first embodiment of a clamp 10 pursuant to the invention. The clamp 10 consists of a first clamping assembly 20, a second clamping assembly 30 and a central shaft 40 which is positioned through bores 21, 22, 31 and 32 within the two clamp assemblies 20, 30 along the longitudinal axis 46 of shaft 40. The specific features of the bores 21 and 22 will be explained in connection with further Figures.

The shaft 40 is preferably a locking unit adapted to allow closing the clamp assemblies 20 and 30. Shaft 40 enters a first jaw 11 through a locking element 50 and a washer 41. The shaft 40 comprises a head 42, a proximal portion 43 and a reduced diameter portion 44 which is followed by a thread portion 49. The outer threaded portion 49 is adapted to be screwed into a complementary inner thread within the distal jaw 14 so that turning the head 42 of the shaft 40 changes the longitudinal position of the shaft 40 against the jaws 11, 12, 13 and 14, which allows opening or closing the entire clamp 10 against the force of a spring 15 provided between the two clamp assemblies 20 and 30. Spring 15 is preferably positioned in corresponding reception counterbores 23 in the jaws 12 and 13. Instead of a spring 15, provided around shaft 40, it is possible to provide a different spring element as Belleville washers or an elastic compressible solid or foam. Upon closing of the clamp assemblies 20 and 30, the jaws adjacent to the spring 15 can eventually come into contact and then the anti-rotation surface 45 which is provided in both surfaces of the jaws 12 and 13 is fixing the angular orientation of each clamping assembly 20 and 30 against the other.

It is noted that a simple clamp according to the invention only comprises one clamping assembly 20 with two jaws and 12 together with the spring element 15 and the central shaft 40 and of course the locking element 50 which function will be described later on. The spring element 15 is preferably but not necessarily positioned between the two clamping assemblies 20 and 30. It can also be provided between the lower jaws 13 and 14. It is important that the spring 15 is not distal to the second jaw 12.

In the embodiment shown in the drawings, after having mounted the shaft 40 with the thread 49 within the jaw 14, the end portion of the thread 49 extending in the distal end portion (see FIG. 3) of the jaw 14 is destroyed through pressure to ensure that the shaft 40 cannot be removed from the clamping assemblies 20, 30. This enables maintaining the clamp 10 as one single piece. It is also possible to provide a jam nut or a nut/counter nut combination on the thread 49 in the distal end portion and recess 47.

Each clamping assembly 20 or 30 comprises two opposing pairs of clamping jaws 11, 12 and 13, 14, respectively. These jaws are essentially similarly shaped on the sides facing each other beside a pin 19 which extends into a corresponding bore 18. This pin-bore connection which is oriented along the longitudinal axis 46 of the clamping device 10 is an anti-rotation device for the jaws 11, 12 and 13, 14, so that these jaws within one pair cannot change their mutual angular orientation. It is possible but not necessary that the pin 19 or the bore 18 receives an elastic fitting piece allowing elastic movements of the pin 19.

The plane surface of jaw 11 or 14 facing the plane surface of jaw 12 or 13 is provided with three spacers 17 arranged in the corners of said surface. The spacers 17 have a mostly triangular form and a height to allow the function of a counter bearing as explained below. Additionally, the spacers 17 allow that the two plane surfaces of the jaws 11, 12 or 13, 14 are in a distance one from the other so that the inter-jaw cavity 66 between these surfaces can be cleaned more easily.

The jaws are provided here with three grooves 61, 62 and 63. Grooves 61, 62 and 63 are all provided in a same plane perpendicular to the longitudinal axis of shaft 40. In that plane they are oriented perpendicular to the radial direction from the center of the bore 21, 22, 31 or 32.

Each pair of grooves 61, 62 or 63, respectively, in each jaw defines one reception cavity formed as a rounded semi-spherical recess in section to provide reception cavities 71, 72 and 73 (see FIG. 2) to allow accommodating cylindrical pins or rods with a defined diameter and to secure them, when the clamp is closed. In the embodiment shown all three grooves 61, 62 and have different sizes so that the corresponding reception cavity 71, 72 and 73 have three different sizes. In other words each reception cavity 71, 72 or 73 is adapted to accept a different fixation element, i.e. a rod, screw, pin or wire having a different diameter. One preferred embodiment of the first clamping assembly 20 has grooves to accept fixation elements having a diameter of 12 mm, 8 mm and 5 mm, respectively. A different embodiment may have a sequence of diameters of 8 mm, 6 mm and 4 mm, respectively.

The second clamping assembly 30 according to the embodiment of FIG. 1 also comprises two jaw portions 13 and 14 and these comprise three grooves 61, 62, 63.

It is of course also possible that the clamping assemblies 20 and 30 are traditional clamping assemblies as shown in EP 0 700 664 having one reception for each pair of jaws. As mentioned above it is also possible to apply the principles of the invention to a device having only one pair of jaws for one single rod and additional functional parts.

Figure 2:
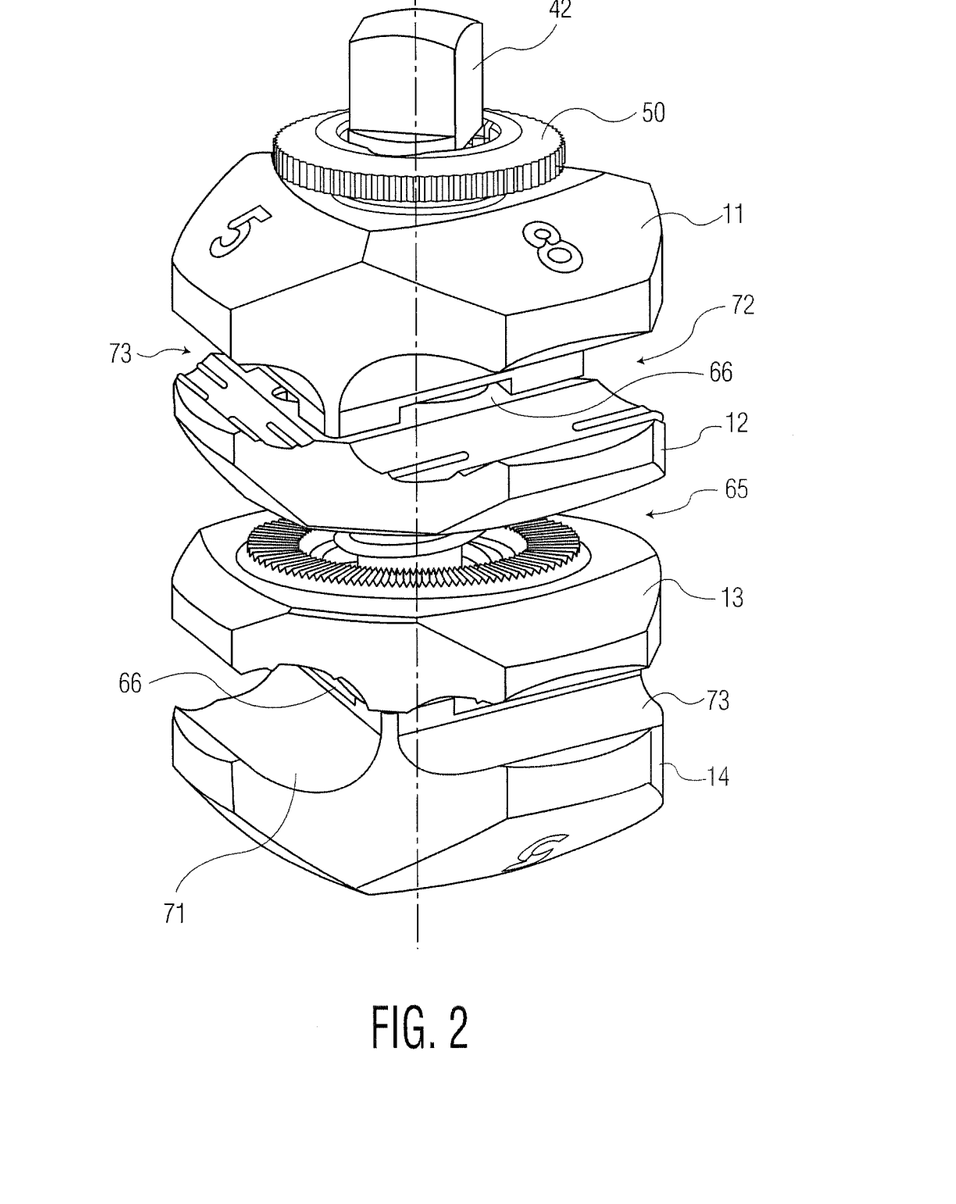
FIG. 2 shows a perspective view of the assembled clamp according to FIG. 1.

FIG. 2 shows a perspective view of the clamp according to FIG. 1. All identical or similar features have received identical reference numerals throughout all drawings and over all different embodiments.

In addition to the different parts shown in FIG. 1 the assembled clamp as shown in FIG. 2 clearly shows the inter-clamp assembly cavity 65 between the two pairs of jaws and the inter-jaw cavity 66, defined through the spacers 17. These cavities 65 and 66 are already difficult to clean, also in view of the hidden counterbore 23 for the spring 15 and especially for bores 21, 22, 31 and 32. since the bores are completely sealed in the case of the threaded end 49 of the shaft 40 and in view of the spring action for the jaw 11 pushing against the head 42 of the shaft. In the embodiment there is provided a washer 41 and a locking element 50 between the head 42 and the jaw 11.

Figure 3:
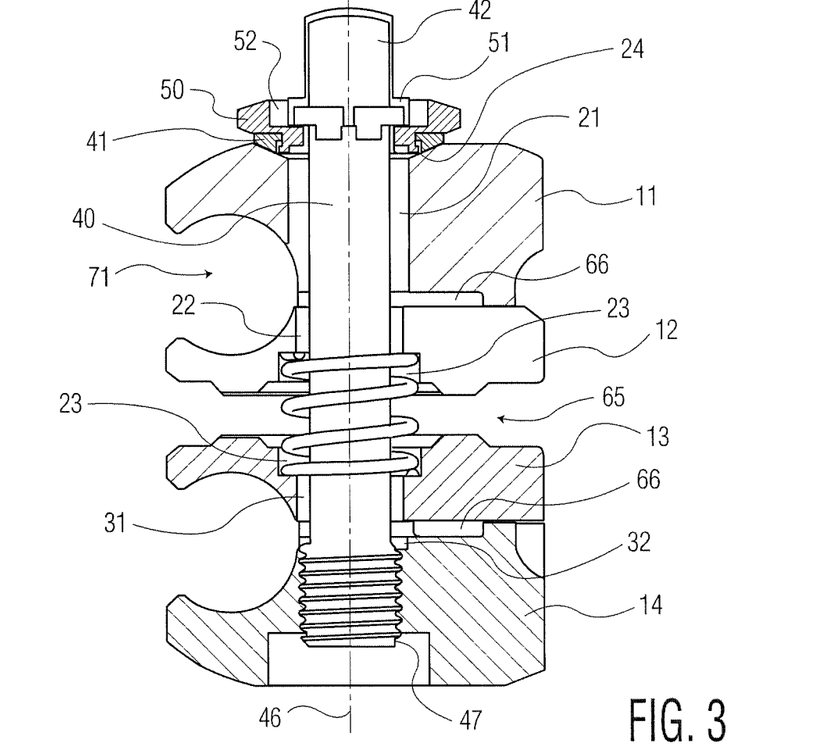
FIG. 3 shows a cross-section along lines 3-3 of FIG. 2 of the clamp according to FIG. 1.

FIG. 3 shows a cross-section of the clamp according to FIG. 1, wherein the clamp 10 is shown in a premounted state, i.e. the spring 15 is under tension. The upper jaw 11 of the first clamping assembly 20 is therefore pushing the rounded washer 41 against an underside of the locking element 50 which in turn pushes with the surface of its locking reception 52 against the underside of the locking nose 51 within the head 42 of shaft 40. The jaw 11 has at the proximal end and around its bore a rounded recess 24 to accommodate the washer 41. This enables a pivoting movement of the upper jaw 11 against the axis of the shaft 40, since the shaft 40 comprises a reduced diameter portion 44 extending over the whole length of the jaws 11, 12 and preferably in jaws 13, 14 in both assemblies 20 and 30. It is also possible that there is no play between shaft 40 and jaw 12; the bore 22 just allowing the introduction of the shaft 40 with preferably some play. Then jaw 12 can only effect a translatory movement along the axis 46.

The shaft 40 as part of a locking element is threaded into the lower distal jaw 14 of the second clamping assembly 30 and the thread 49 is destroyed. A different possibility is to use a counter nut avoiding withdrawal of the shaft 40. Therefore the two clamp assemblies 20, 30 can be opened and closed through turning the head 42 of shaft 40 and thus turning shaft 40 with a blocking feature (destroyed end of the thread or use of a counter nut) in the jaw thread.

The combination of shaft 40 and counter nut can also be replaced by a single screw to be screwed into the lower jaw 14 of the second clamping assembly 30. Threading may be provided in the bore or the screw may exhibit self-tapping threading. Quite generally, a locking unit may be provided which may be a lever locking unit or a bayonet lock. Among these locking units supporting disks or toothed disks can be chosen, which, for the sake of simplicity, are not shown in the drawings.

It is clear that withdrawal of the shaft 40 along the axis 46 using the maximum possible thread length does not provide a real interstitial space for cavities 65 and 66.

Figure 4:
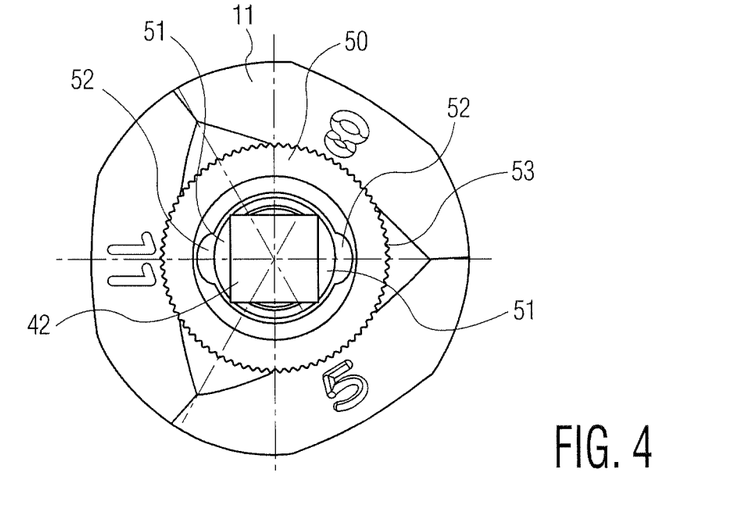
FIG. 4 shows a top view of the clamp according to FIG. 1.

FIG. 4 shows a view from above on the clamp according to FIG. 1. Since the embodiment of FIG. 1 comprises three grooves 61, 62 and 63, there are three side walls for jaw 11, which provide, when looked from above as in FIG. 4 a triangular shape of each clamping assembly 20 or 30.

Figure 5:
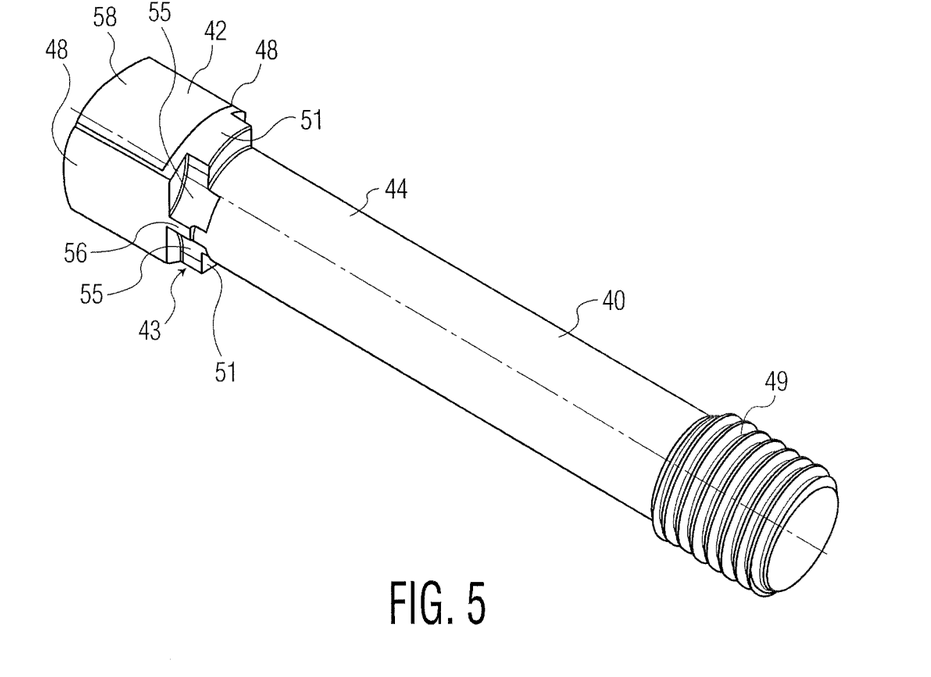
FIG. 5 shows a perspective view of a shaft of the clamp according to FIG. 1.

FIG. 5 shows a perspective view of the shaft 40 of the clamp according to FIG. 1. Beside the features mentioned in connection with the other drawings, the proximal area 43 of the shaft 40 is unique. It comprises two diametrally opposing locking noses 51, extending beyond the reduced diameter shaft portion 44. In addition to these locking noses 51 there are rounded recesses 55. As can be seen from FIG. 5, these recesses allow for a small transition section 56 not essentially extending beyond the reduced diameter 44 of the shaft 40. Additionally the flat side surfaces 48 of the head 42, being a four cornered shaft, are flush with the respective transition sections 56.

Figure 6:
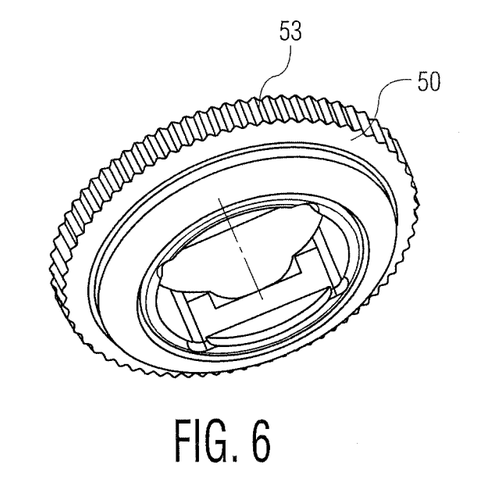
FIG. 6 shows a perspective view from below on a locking element of the clamp according to FIG. 1.
Figure 7:
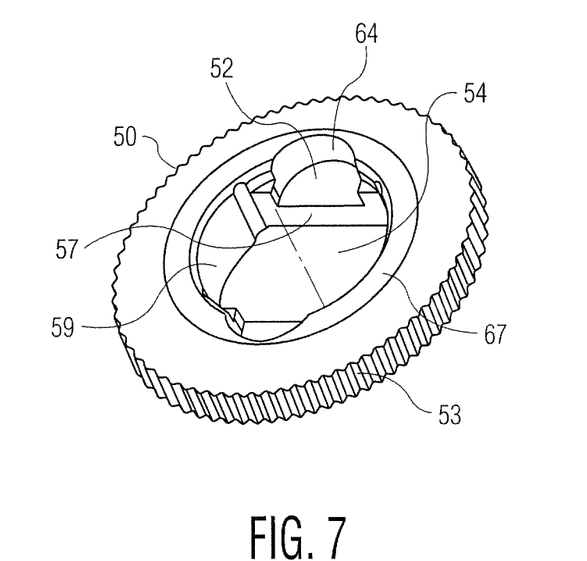
FIG. 7 shows a perspective view from above on the locking element according to FIG. 6.
Figure 8:
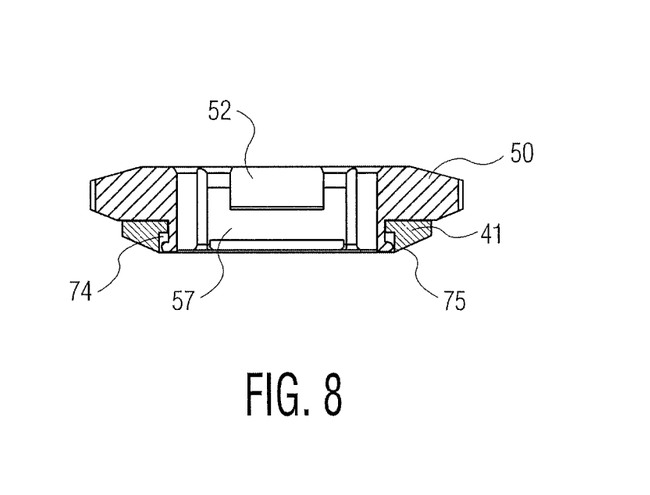
FIG. 8 shows a cross-section of the locking element according to FIG. 6 in connection with a washer.

FIG. 6 shows a perspective view from below on the locking element 50 of the clamp 10 according to FIG. 1 together with the washer 41 as explained below. FIG. 7 shows a perspective view from above on the locking element according to FIG. 6. FIG. 8 shows a cross-section of the locking element according to FIG. 6 in connection with washer 41. The locking element 50 comprises a thumb wheel 53 for easy turning of element 50 around the axis 46 of the shaft. The locking element 50 has a through bore hole 54 with specific dimensions. Through bore hole 54 is delimited on opposing sides by surfaces 57 parallel to the axis 46 wherein the delimitation are when viewed from above—chords of a circle.

Surfaces 57 are at a distance one from another to allow the passage of the flat head surfaces 48 of the head 42 of the shaft 40. The further side surfaces 59 of the through bore hole 54 are—in a view from above—circular arcs. These allow the passage of the rounded surfaces 58 of the four cornered head 42, i.e. comprising locking noses 51. The further side surfaces 59 define a cavity allowing passage of the head 42.

The underside locking element 50 comprises a flange 74 allowing the introduction of a corresponding inner circumferential locking flange of washer 41. Washer 41 can also be incorporated into locking element 50. Washer 41 provides the inclined bearing surface 75 on the underside for a non-translational movement of upper jaw 11.

The rounded form of locking element 50, together with the washer 41, allows a rotation around the longitudinal axis 46 of the device. Within such a rotation several positions have a specific function. Locking element 50 can take the position as in FIG. 1, within which the locking noses 51 of head 42 of the shaft 40 are lodged within locking receptions 52 of the element 50. Since there are two diametrically opposed noses and receptions two identical position can be reached by turning the element by 180 degrees. The same function can be obtained, if in other embodiments there is provided only one nose-reception pair or a set of three (e.g. in an angle of 120 degrees).

Within this or these positions, called locked positions, head 42 of shaft 40 is in a position that its cross-section cannot pass the through borehole 54 of the locking element. The locking function of the shaft and screw in view of the clamping function of the device as explained above is obtained. Turning head 42 open or closes the set of jaws 11, 12 and 13, 14 as within traditional clamping devices. Since locking element 50 is in positive locking with head 42, the element 50 rotates with shaft 40.

There are one or more different positions, called open positions, within which head 42 of shaft 40 is in a position that its cross-section can pass the through borehole 54 of the locking element. The flat sides 48 of head 42 pass near surfaces 57 and the rounded head surfaces 58 pass near the circular arc surfaces 59. The locking function of the shaft and screw in view of the clamping function of the device is removed. Therefore the locking element 50 can be removed. This result can also be obtained with one nose-reception pair or e.g. three nose-receptions pairs. Of course symmetric arrangement of these pairs is preferred to avoid torsional moments acting on the elements.

Locking element 50 comprises a defined height, especially visible within the side wall 64 around the locking reception 52. Therefore locking element 50 cannot be turned as such in order to move locking element 50 from the closed position to the open position, but there is an actuation height provided by side wall 64. It is noted that the spring 15 urges the locking element from below against the locking noses 51 of the head 42. The removal of locking element 50 necessitates the loosening of the screw of shaft 40 to obtain space for a translational movement of locking element 50 and jaws 11 and 12. Then locking element 50 can be pressed down along the axis 46 while head 42 of shaft 40 is held. Locking nose(s) 51 of the head then leave locking receptions 52 defined by their side walls 64 and once noses 51 come free, thumb wheel 53 can be used to rotate locking element 50, while locking noses 51 are gliding on the counter surface 67 of the locking element 50. After a rotation of 90 degree the surfaces 48 and 57 as well as 58 and 59 are aligned and the locking element 50 can be removed along the axis 46.

This removal of locking element 50 allows further handling of the device as explained in connection with FIG. 3. The uppermost jaw 11, or in different embodiments: the part of the clamping device 10 being adjacent to locking element 50, comprises a through bore 21 accommodating shaft 40 of the clamping device, and through bore 21 has a larger diameter than the maximum diameter of head 42 of shaft 40. This allows complete withdrawal of first jaw 11 from the shaft axis. The bore 22 of second jaw 12 has a smaller diameter than the maximum diameter of head 42 of the shaft 40. Therefore, upon removal of the first jaw, second jaw 12, pushed by spring 15 against head 42, remains on shaft 46 of clamping device 10. Nevertheless, the inter-clamp assembly cavity 65 and the inter-jaw cavity 66 (between the jaws 13 and 14) can now be cleansed and also the reception space of the spring is easily reached. This partly disassembly enables easier cleansing and sterilization.

It is noted that it is not mandatory, that the diameter of the so called reduced diameter portion 44 of the shaft 40 is reduced for its entire length, although preferred. The reduced diameter is necessary in the area where second jaw 12 is intended to move upon removal of first jaw 11 and it is necessary in the area where locking element 50 is intended to be placed. It is however possible to provide e.g. ribs on shaft 40, just beyond the locking element and where the rounded recess 24 of the first jaw is located, for stabilization of a pure translational movement of first jaw 11, although this is usually not preferred. The jaws 12 and 13 as well as spring 15 can be mounted on shaft 42 from its distal end, i.e. over the threaded part 49 having a lesser diameter than the bore of jaws 12 and 13 and the inner opening of spring 15.

Figure 9:
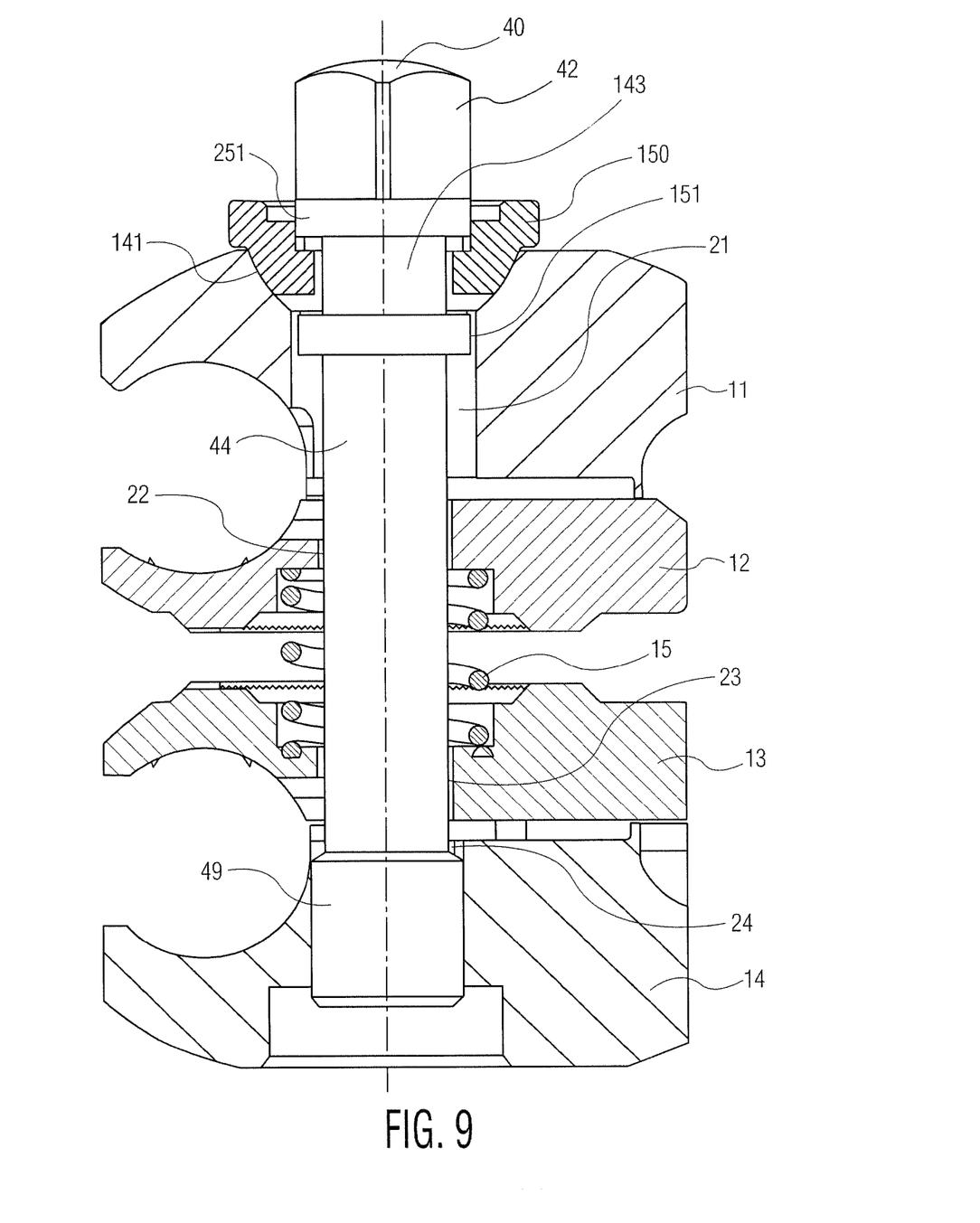
FIG. 9 shows a cross-section of a second embodiment of the clamp of the present invention.
Figure 10:
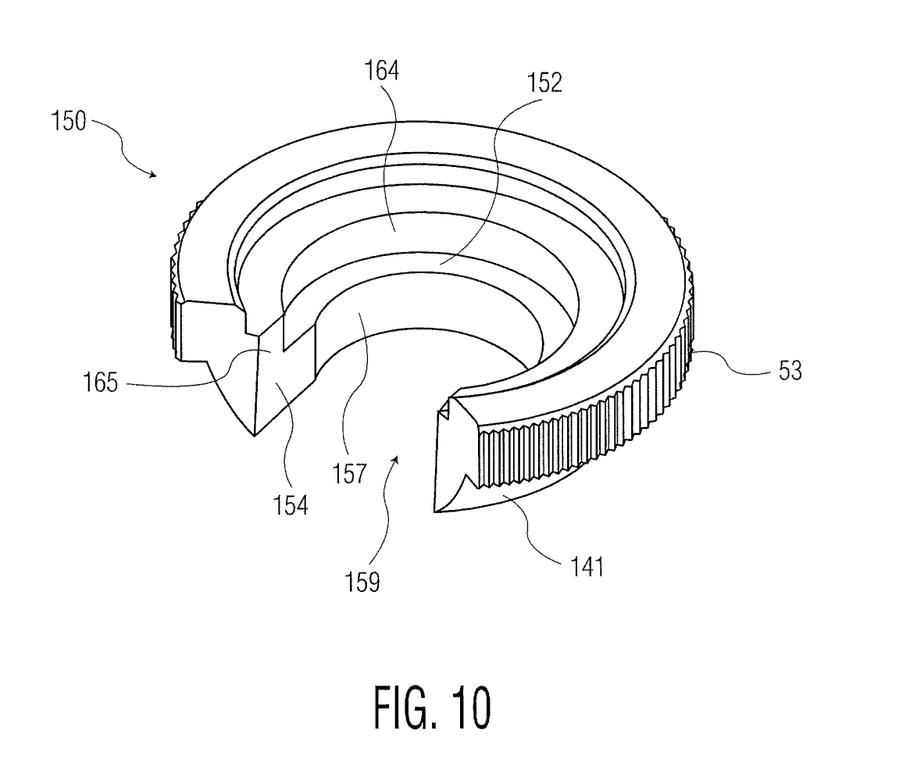
FIG. 10 shows a perspective view from above on the locking element of the clamp according to FIG. 9.

FIG. 9 shows a cross-section of a second embodiment of a clamp 100 of the present invention. The following description only relates to features of this clamp 100 which are different in view of clamp 10. The other features are identical to the corresponding features of clamp 10 and have received the same reference numerals. FIG. 10 shows a perspective view from above on the locking element 150 of the clamp according to FIG. 9.

Jaw 11 of clamp 100 has an inner bore 21 for accommodating shaft 40, which bore 21 has a larger diameter than the diameter of bore 22 of jaw 12 as in the first embodiment. In the embodiment shown the shaft 40 comprises a flange 151 having a larger diameter than the reduced diameter portion 44 allowing passage of the jaw through bore 21 but blocks jaw 12. The head of shaft 40 has a similar diameter, but this is not mandatory. As it will be explained in the following, head 42 can also have a quite smaller diameter, depending on the diameter of the proximal portion 143 of the shaft 40, in combination with the locking element 150.

Locking element 150 is not a closed ring but comprises a side opening 159. The inner diameter of the ring defines an inner circular surface 157 for definition of the through-bore. The side surfaces 154 of the opening 159 are spaced at a smaller distance than the diameter of the through-bore, especially the distance of side surfaces 154 one from the other is smaller than the diameter of shaft 40. This allows clicking into place of shaft 40. The underside 141 of locking element 150 incorporates the inclined surface of washer 41 of the first embodiment. The inner circular surface 157 ends adjacent to a locking rim 152 defining a flange surface of locking element 150 to be pushed by action of spring 15 through the jaws 12 and 11 against the underside of head 42. This locks the clamping device, when the locking element is in place. In order to remove jaw 11 locking element 150 has to be removed beforehand as within the first embodiment.

Locking element 150 cannot be removed directly since the open side 159 of the element 150 surrounded by its underside 141 is also maintained by jaw 11. Therefore, the screw 40 has to be loosened to allow jaw 11 to be pushed away from the locking element. Additionally, the locking rim 152 is adjacent to the side wall 164, so that it is also necessary to loosen the screw for this additional height, since the blocking surface 165 as part of the side surface 154 does not allow the lower portion 251 of the head 42 to be pushed out sidewards from the locking element 150.

It is noted that either a portion 51 or 251 of the head 42 or a portion 151 separate and beyond a transitional zone 143 has a larger diameter than the bore 22 of the second jaw wherein in case of a larger diameter of the transitional zone 143 then the head 42 can have a smaller diameter so long as to allow blocking noses 51 or flanges 251 of the head 42 to be engaged by a abutment surface 52 or 152, respectively.

Figure 11:
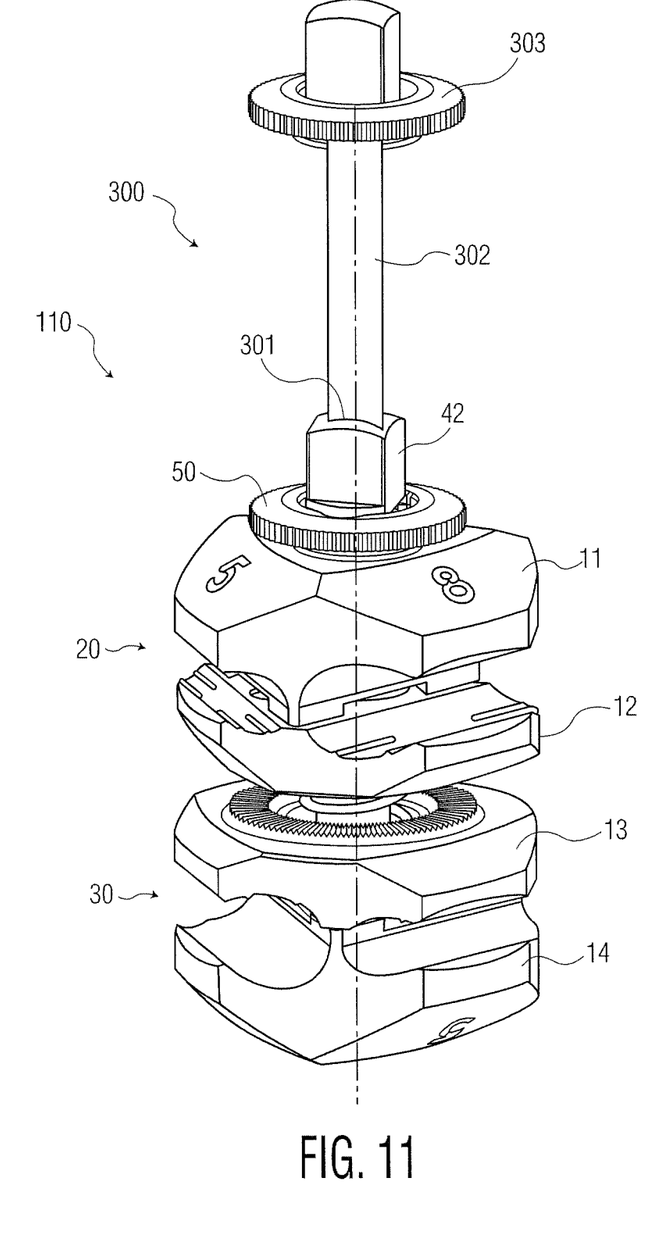
FIG. 11 shows a perspective view of a third embodiment of the clamp of the present invention.

FIG. 11 shows a perspective view of a third embodiment of a clamp 110 of the present invention. First clamping assembly 10 and second assembly 20 of this clamping device 110 are e.g. identical with the corresponding clamping assembly of the embodiment of FIG. 1. It is a further optional embodiment, if there diameters of the bores accommodating the shaft 40 are different to the embodiment of FIG. 1. Bore 22 within jaw 12 and bore 31 within jaw 13 may have a similar large diameter as has bore 21 in jaw 11. When bores 22 and 31 have a larger diameter than the maximum diameter of the head 42 of the shaft 40, withdrawal of the second 12 and third jaw 13 from the shaft axis is also possible.

The embodiment according to FIG. 11 comprises an additional blocking tool. FIG. 11 shows blocking tool 300 to be used in connection with the clamping assemblies clamping assemblies and the device according to the invention as described above. The head 42 of shaft 40 comprises an inner opening 301 having a thread, within which the outer thread of the blocking tool 300 can be fixed. It would also be possible that blocking element 300 is clipped onto the head 42 or comprises a bayonet coupling. The blocking tool 300 further comprises a shaft 302 adjacent to the outer thread 301 and a blocking flange 303 at the other free end. The diameter of the shaft 302 is preferably smaller or equal to the diameter of the reduced diameter portion 44. The diameter of the blocking flange 303 is larger then the through-bore 54 of the locking element and the corresponding bore 21 of the jaw 11. It is then possible, prior to cleansing, to loosen the shaft 40 as an preparation of removal of the locking element 50 and the first jaw 11, then to fix the blocking tool 300 on head 42 of shaft 40, and finally to withdraw locking element 50 and the first jaw 11 as explained above on the shaft. However, now these elements are blocked on the extended axis 46 of the screw and thus the elements can be cleansed easily without losing the first jaw. In the above mentioned embodiment with a larger diameter section of bore 22 and 31, then all jaws 11, 12, 13 as well as spring 15 and blocking element 50 can be cleaned on the long shaft being the sum of shaft 40+shaft 302. In this embodiment the locking unit can be considered to comprise the screw 40 as well as the locking unit 300.

The locking unit 40 is described having a shaft 44 which can be screwed to cause a movement of a blocking part 42, of the locking unit 40 along axis 46. However, it is also possible that the blocking part 42 or 43 comprises a flange acting on an abutment surface of the upper jaw 11 and which flange is actuated by a lever as locking unit.

The provision of a defined height of the side surfaces 64 or 164 ensure that the locking element 50 is not easily lost or displaced in a pre-clamping position of the clamping device 10, i.e. in a position wherein the spring 15 is pushing against the jaw 11 and maintains the locking element 50 in place, but wherein there is no clamping action itself.

The wording diameter of the bore 21 and 22 usually relates to cylindrical bores as well as diameter of the head 42 or diameter of the locking unit 40 usually relate to the diameter of a cylindrical locking unit but also to the largest diameter in case of a non-cylindrical unit as shown in the drawings. It is of course also possible to provide non-cylindrical shafts. In this case larger has the meaning that there exists an orientation of the non-cylindrical shaft allowing the passage of the bore of the corresponding jaw and smaller has the meaning that such an orientation does not exist. Of course the locking element 50 always has a positive locking feature, which allows passage of the element 50 over the head upon appropriate rotation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A clamping device for use in an external fixation system for holding bone fragments adjacent to each other with the help of fixation elements, comprising
at least one clamping assembly having first and second jaws, providing at least one recess to accommodate an element to be clamped along a longitudinal axis of the recess,
a one-piece locking unit having a shaft portion coupled to the second jaw and a head portion, the head portion having a maximum dimension greater than the shaft portion;
a locking element having a through bore;
wherein each of the first and second jaws has a through bore extending along a central axis to accommodate the locking unit shaft portion extending there through, wherein the first jaw is positioned adjacent to the head portion of the locking unit, wherein the head portion of the locking unit is adapted for operating a clamping action abutting against the first jaw to allow the jaws to close, wherein the locking element is mounted between a surface on the locking unit head portion facing the first jaw and a surface on the first jaw, wherein the maximum dimension of the locking unit head portion has a larger diameter than the through bore of the second jaw, wherein the maximum dimension of the head portion of the locking unit has a smaller diameter than the through bore of the first jaw, wherein the locking element comprises at least one locking surface which can be rotated to be selectively brought into and out of positive locking with the surface of the locking unit head facing the first jaw for allowing removal or blocking removal of the locking element from the clamping device.

2. The clamping device according to claim 1, wherein the locking unit comprises a portion separate and beyond the head portion having said larger diameter than the through bore of the second jaw.

3. The clamping device according to claim 1, wherein the at least one locking surface of the locking element comprises an adjacent wall parallel to the through bore central axis of the device and providing an actuation height for disengaging the positive locking.

4. The clamping device according to claim 1, wherein the at least one locking surface of the locking element comprises two or three locking surfaces within an angular spacing of 180 or 120 degree, respectively.

5. The clamping device according to claim 4, wherein the locking element comprises two or three passage allowing surfaces within an angular spacing of 180 or 120 degree, respectively.

6. The clamping device according to claim 1, wherein a locking surface of the locking element comprises a circular locking rim and an adjacent side wall providing the actuation height for disengaging the positive locking.

7. A clamping device for use in an external fixation system comprising:
a first and a second jaw each having a bore therethrough;
a one-piece locking unit comprising a head and a shaft extending through the bore in the first jaw and coupled to the second jaw, the shaft having the head formed thereon, a maximum dimension of the head being smaller than a diameter of the bore in the first jaw and larger than a diameter of the bore in the second jaw, the first jaw positioned closer to the head than the second jaw;
a locking element located between the head and the first jaw, the locking element having an outer diameter greater than the diameter of the bore in the first jaw and an opening for receiving the shaft, the opening having spaced first sidewalls and spaced second sidewalls, the distance between the spaced first sidewalls greater than the maximum dimension the head and the distance between the spaced second sidewalls less than the maximum diameter of the head; and
a means for selectively engaging and disengaging the locking element from the locking unit so that the first jaw can pass over the locking unit head and be removed from the locking unit shaft and head.

8. The clamping device as set forth in claim 7 wherein the head has a coupling element engaged with a coupling element on each of the spaced second sidewalls of the locking element in a first rotational position of the locking element with respect to the shaft and disengaged from the coupling element on the spaced second sidewalls of the locking element in a second rotational position.

9. The clamping device as set forth in claim 8 wherein the head and locking element each have two coupling elements located at 180° about an axis of the shaft.

10. The clamping device as set forth in claim 9 wherein the coupling element on the head and the locking element have mating planar surfaces.

11. The clamping device as set forth in claim 10 wherein the head planar surfaces are spaced apart a distance less than the locking element planar surfaces.

12. The clamping device as set forth in claim 8 wherein the head and locking element each have two coupling elements located at 180° about an axis of the shaft.

13. The clamping device as set forth in claim 7 wherein the head has a coupling element engaged with a coupling element on the locking element in a first rotational position of the locking element with respect to the shaft and disengaged from the coupling element of the locking element in a second rotational position.

14. A clamping device for use in an external fixation system comprising:

a first and a second jaw each having a bore therethrough;

a one-piece locking unit comprising a shaft portion extending through a bore in the first jaw and coupled to the second jaw, the shaft having an integral head portion, a maximum dimension of the head portion being smaller than a diameter of the bore in the first jaw and larger than a diameter of the bore in the second jaw, the first jaw positioned closer to the head than the second jaw, the locking unit head portion having two opposite spaced apart surfaces facing the first jaw;

a locking element located between the surface of the head facing the first jaw, the locking element having an opening for receiving the shaft, the locking element opening defining two opposite spaced apart first surfaces adapted to overlap and engage the two spaced apart surfaces on opposite sides of the locking unit head portion in one rotational position and the locking element having two oppositely spaced apart second surfaces that are spaced apart a distance greater than the opposite spaced apart surfaces of the head allowing passage of the head portion in a second rotation position.

15. A clamping device for use in an external fixation system comprising:

at least one clamping assembly comprising first and second jaws, the jaws having alignable recessed portions for accommodating a rod, pin or ring to be clamped by the first and second jaws, the first jaw having a through bore with a first diameter and the second jaw having a through bore of a second diameter    a locking unit comprising a shaft portion and a head portion, the head portion having a maximum dimension smaller than the first diameter and greater than the second diameter of the first and second jaws, the shaft portion extending through the bore of the first and second jaws    a locking element having a through opening for engaging the locking unit head portion mounted between the first jaw and the locking unit head, the through opening having two first and two second sections alternating around the locking element through openings with the two first sections facing each other and the two second sections facing each other, the two first sections spaced apart a distance greater than the maximum dimension of the locking unit head portion, the two second sections spaced apart a distance less than the maximum dimension of the locking unit head portion whereby rotation of the locking element 90° moves the maximum locking unit head dimension from engagement with the second section allowing removal of the locking element from the locking unit and passage of the first jaw over the locking unit head portion.

* * * * *